US005939063A

United States Patent [19]
Vadas et al.

[11] Patent Number: 5,939,063
[45] Date of Patent: Aug. 17, 1999

[54] MODIFIED FORMS OF GRANULOCYTE MACROPHAGE-COLONY STIMULATING FACTOR AS ANTAGONISTS

[75] Inventors: Mathew Alexander Vadas, Stirling; Angel Francisco Lopez, North Adelaide; Mary Frances Shannon, Crafers, all of Australia

[73] Assignee: Medvet Science Pty. Ltd., South Australia, Australia

[21] Appl. No.: 08/591,438

[22] PCT Filed: Jul. 28, 1994

[86] PCT No.: PCT/AU94/00432

§ 371 Date: Apr. 8, 1996

§ 102(e) Date: Apr. 8, 1996

[87] PCT Pub. No.: WO95/04075

PCT Pub. Date: Feb. 9, 1995

[30] Foreign Application Priority Data

Jul. 28, 1993 [AU] Australia ............................... PM 0186
Mar. 30, 1994 [AU] Australia ............................... PM 4772

[51] Int. Cl.⁶ .......................... A61K 38/19; C07K 14/535
[52] U.S. Cl. ........................ 424/85.1; 530/351; 435/69.5; 435/71.2; 435/471; 435/325; 435/252.3; 435/320.1
[58] Field of Search ........................... 530/351; 424/85.1; 435/69.5, 71.1, 71.2, 172.3, 252.3, 320.1, 471, 325

[56] References Cited

FOREIGN PATENT DOCUMENTS

WO89/10403 11/1989 WIPO .

OTHER PUBLICATIONS

Gough et al. (1984) Nature, vol. 309, pp. 763–767.
J.F. Bazan (1990) "Haemopoietic Receptors and Helical Cytokines" *Immunology Today* 11:350–54.
B.J. Brandhuber et al. (1987) "Three–Dimensional Structure of Interleukin–2" *Science* 238:1707–1709.
M. A. Contreras et al. (1983) "Iodine Monochloride (IC1) Iodination Techniques" *Methods in Enzymology* 92:277–292.
M.J. Elliott, et al. (1990) "IL–3 and Granulocyte–Macrophage Colony–Stimulating Factor Stimulate Two Distinct Phases of Adhesion in Human Monocytes" *The Journal of Immunology* 145(1):167–176.
J.C. Gasson, et al. (1986) "High–Affinity Binding of Granulocyte–Macrophage Colony–Stimulating Factor to Normal and Leukemic Human Myeloid Cells" *Proc. Natl. Acad. Sci. USA* 83:669–673.
D.P. Gearing, et al. (1989) "Expression Cloning of a Receptor for Human Granulocyte–Macropahge Colony–Stimulating Factor" *The EMBO Journal* 8(12):3667–3676.
J. Ghrayeb et al. (1984) "Secretion Cloning Vectors in *Escherichia coli*" *The EMBO Journal* 3(10):2437–2442.
G.J. Goodall, et al. (1993) "A Model for the Interaction of the GM–CSF, IL–3 and IL–5 Receptors with their Ligands" *Growth Factors* 8:87–97.

K. Hayashida, et al. (1990) "Molecular Cloning of a Second Subunit of the Receptor for Human Granulocyte–Macrophage Colony–Stimulating Factor (GM–CSF): Reconstitution of a High–Affinity GM–CSF Receptor" *Proc. Natl. Acad. Sci. USA* 87:9655–9659.
D. Koshland et al. (1980) "Secretion of Beta–Lactamase Requires the Carboxy End of the Protein" *Cell* 20:749–760.
U.K. Laemmli, et al. (1970) "Cleavage of Structural Proteins During the Assembly of the Head of Bacteriophage T4" *Nature* 227:680–685.
A.F. Lopez, et al. (1986) "Recombinant Human Granulocyte–Macrophage Colony–Stimulating Factor Stimulates In Vitro Mature Human Neutrophil and Eosinophil Function, Surface Receptor Expression, and Survival" *J. Clin. Invest.* 78:1220–1228.
A.F. Lopez, et al. (1988) "Recombinant Human Interleukin–3 Stimulation of Hematopoiesis in Humans: Loss of Responsiveness With Differentiation in the Neutrophilic Myeloid Series" *Blood* 72(5):1797–1804.
A.F. Lopez, et al. (1992) "Residue 21 of Human Granulocyte–Macrophage Colony–Stimulating Factor is Critical for Biological Activity and for High But Not Low Affinity Binding" *The EMBO Journal* 11(3):909–916.
J.H. Morrissey et al. (1981) "Silver Stain for Proteins in Polyacrylamide Gels: A Modified Procedure with Enhanced Uniform Sensitivity" *Analytical Biochemistry* 117: 307–310.
D.A.D. Parry, et al. (1988) "Conformational Homologies Among Cytokines: Interleukins and Colony Stimulating Factors" *Journal of Molecular Recognition* 1(3):107–110.
H. Towbin, et al. (1979) "Electrophoretic Transfer of Proteins from Polyacrylamide Gels to Nitrocellulose Sheets: Procedure and Some Applications" *Proc. Natl. Acad. Sci. USA* 76:4350–4354.
G.G. Wong et al. (1985) "Human GM–CSF: Molecular Cloning of the Complementary DNA and Purification of the Natural and Recombinant Proteins" *Science* 228:810–815.
M.J. Zoller et al. (1984) "Oligonucleotide–Directed Mutagenesis: A Simple Method Using Two Oligonucleotide Primers and a Single–Stranded DNA Template" *DNA* 3(6):479–488.
S.M. Zurawski, et al. (1989) "Mouse Interleukin–2 Structure–Function Studies: Substitutions in the First α–Helix Can Specifically Inactivate p70 Receptor Binding and Mutations in the Fifth α–Helix Can Specifically Inactivate p55 Receptor Binding" *The EMBO Journal* 8(9):2583–2590.

*Primary Examiner*—Prema Mertz
*Attorney, Agent, or Firm*—Scully, Scott, Murphy & Presser

[57] ABSTRACT

The present invention relates to modified and variant forms of haemopoietic growth factors (HGF) capable of acting as antagonists to the corresponding native haemopoietic growth factors and their use in ameliorating aberrant effects caused by the native molecules. A modified haemopoietic growth factor (HGF) is characterized by being in unglycosylated form and comprising a sequence of amino acids within a first α-helix wherein one or more exposed amino acids in said first α-helix having acidic or acidic-like properties are substituted with a basic amino acid residue. The preferred HGF are granulocyte-macrophage colony-stimulating factor (GM-CSF), interleukin (IL)-2, IL-3, IL-4, IL-5, IL-6, IL-7, IL-9, IL-10, G-CSF and erythropoietin (EPO).

9 Claims, 13 Drawing Sheets

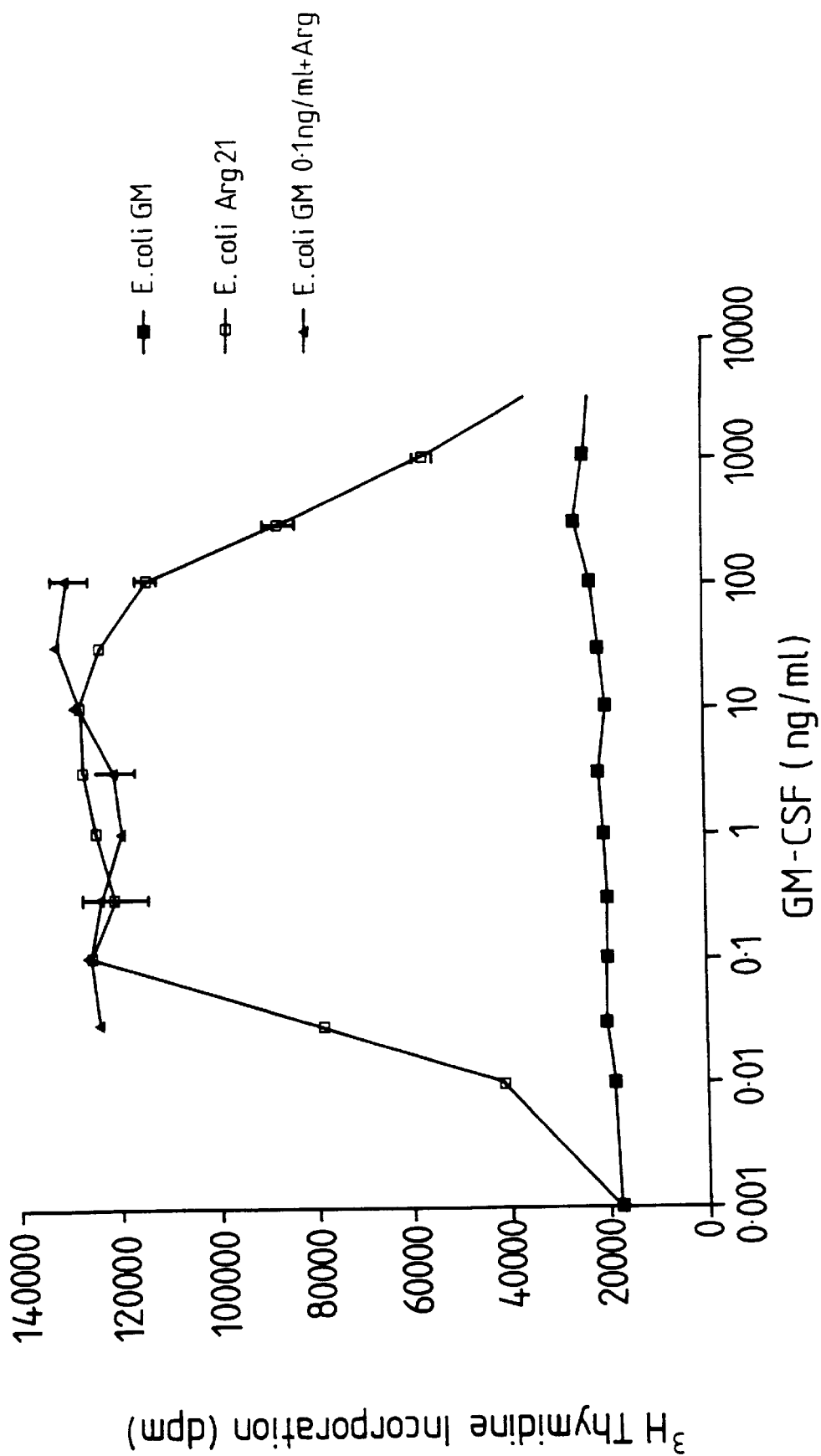

MODIFIED FORMS OF GRANULOCYTE MACROPHAGE-COLONY STIMULATING FACTOR AS ANTAGONISTS

CROSS REFERENCE TO RELATED APPLICATION

This is a 371 of PCT application PCT/AU94/00432, filed Jul. 28, 1994.

The present invention relates to modified and variant forms of haemopoietic growth factors capable of acting as antagonists to the corresponding native haemopoietic growth factors and their use in ameliorating aberrant effects caused by the native molecules.

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Granulocyte-macrophage colony-stimulating factor (GM-CSF) is one member of a family of haemopoietic growth factors (HGFs) which have a similar predicted tertiary configuration (Parry et al, 1988) and whose receptors also belong to a common family (Gearing et al, 1989, Bazan, 1990). This family of haemopoietic growth factors includes, for example, in addition to GM-CSF, the cytokines IL-2, IL-3, IL-5, IL-6 and IL-10. A distinct subfamily comprising GM-CSF, IL-3 and IL-5 can be discerned based on structural similarities (Goodall et al, 1993) and on their ability to interact with a common receptor component (Lopez et al, 1992).

Human GM-CSF (hGM-CSF) comprises 127 amino acids and is available in recombinant form (rhGM-CSF). The hGM-CSF receptor has also been cloned and shown to comprise a binding ($\alpha$) chain exhibiting low affinity binding to GM-CSF (Gearing et al, 1989) and a second ($\beta$) chain which does not measurably bind GM-CSF by itself but it allows the formation of a high affinity receptor when co-expressed with the $\alpha$ chain (Hayashide et al, 1990).

GM-CSF exhibits a range of activities extending over neutrophil, eosinophil and monocyte lineages. Specifically, GM-CSF stimulates the progenitors of these cells to proliferate and differentiate to become mature cells. In addition, it stimulates mature cells to greater function. The stimulation of mature cells results in greater capacity to phagocytose and kill micro-organisms, kill antibody-coated tumour cells and parasites and generate superoxide anion ($O_2^-$) in response to various stimuli. The purpose of this activation is presumed to enable the mature cells to become better effector cells in inflammatory reactions.

Therapeutically, the HGFs form an important group of molecules for their actual or potential properties. For example, the main indications for GM-CSF are for its effects on progenitor cells or mature cells. Using its effects on progenitor cells, GM-CSF is used in the treatment of bone marrow failure as seen in aplastic anaemia or chemotherapy or AIDS-induced marrow suppression. In the treatment of infections, the capacity to stimulate mature cells is especially relevant. The capacity of GM-CSF-activated neutrophils and eosinophils to kill tumour cells that have bound antibody is especially remarkable and could be used in tumour therapy.

However, despite the actual and potential benefits of HGFs, they can exhibit some detrimental side effects. For example, GM-CSF can exhibit toxicity due to stimulation of mature cells causing blood vessel damage or thrombosis. The eosinophilia caused by GM-CSF appears especially damaging in this regard. The molecule can also have detrimental effects by stimulating growth of leukaemia cells and tumour cells of non-haemopoietic origin and stimulating production of inflammatory mediators.

International Patent Application No. PCT/AU89/00177 and an article by Lopez et al. (1992) disclose amino acid variants of GM-CSF which have exhibited reduced potency. These variants were investigated further for their potential as GM-CSF antagonists. However, the variants cause classical stimulation at concentrations 100 fold greater compared to the native GM-CSF molecule. Furthermore, attempts to find antagonistic properties failed since mixing large concentrations of one of the variants with suboptimal concentrations of native GM-CSF resulted in stronger GM-CSF stimulation with no evidence of inhibition being observed.

There is a need, therefore, to develop antagonists to HGFs and in particular GM-CSF which are capable of ameliorating the aberrant effects of the corresponding native molecules. There is also a need for such antagonists not to exhibit agonist properties in respect of the corresponding HGFs.

Accordingly, one aspect of the present invention provides a haemopoietic growth factor characterised by being in unglycosylated form and comprising a sequence of amino acids within a first $\alpha$-helix wherein one or more exposed amino acids in said first $\alpha$-helix having acidic or acidic-like properties are substituted with a basic amino acid residue.

In accordance with the present invention, it is proposed that the modified HGFs defined above act as antagonists of the native form of the corresponding HGF but not other HGFs. The term "modified" is considered herein synonymous with terms such as "variant", "derivative" and "mutant".

The HGFs are preferably GM-CSF, IL-2, IL-3, IL-4, IL-5, IL-6, IL-7, IL-9, IL-10, granulocyte colony-stimulating factor (G-CSF) and erythropoietin (EPO) modified in accordance with the present invention. Most preferably, the HGF is GM-CSF. The HGFs are preferably in recombinant or synthetic form and, with the exception of the amino acid substitution(s) in the first $\alpha$-helix, the amino acid sequence of the HGF may be the same as the naturally occurring molecule (i.e. native molecule) or may carry single or multiple amino acid substitutions, deletions and/or additions to the native amino acid sequence. The HGF sequences are preferably of mammalian origin such as from humans, livestock animals, companion animals or laboratory test animals. Most preferably, the HGFs are of human origin or of a mammalian origin capable of functioning in humans.

The first $\alpha$-helix of GM-CSF has been determined at 2.4 angstrom resolution by X-ray crystallography and encompasses amino acid residues 13 to 28. Similar procedures may be adopted to determine the first $\alpha$-helix in other haemopoietic growth factors. The position may also be determined by analogy to GM-CSF structure.

Reference to "unglycosylated form" herein means that the molecule is completely unglycosylated such as when expressed in recombinant form in a prokaryotic organism (e.g. E. coli). Alternatively, a glycosylation-deficient mammalian cell may be used or complete deglycosylation may occur in vitro using appropriate enzymes. Accordingly, the present invention extends to chemically synthesised GM-CSF which is in unglycosylated form.

An "exposed" amino acid is taken herein to refer to an amino acid on an exposed or outer portion of an $\alpha$-helix compared to those amino acids orientated towards the inside of the molecule.

An acidic amino acid includes, for example, Glu and Asp. Preferred basic amino acids are Arg and Lys.

According to another aspect of the present invention, there is provided a haemopoietic growth factor characterised by:

(i) being in unglycosylated form;
(ii) comprising a sequence of amino acids within the first α-helix;
(iii) one or more exposed amino acids in said α-helix which have acidic or acidic-like properties being substituted by a basic amino acid residue;
(iv) being in recombinant or synthetic form;
(v) being capable of acting as an antagonist for at least one property of the corresponding native HGF.

This aspect of the present invention is predicated in part on the surprising discovery that a mutation in amino acid 21 (Glu) of hGM-CSF to Arg or Lys together with the variant in GM-CSF being in unglycosylated form results in the hGM-CSF valiant being unable to detectably exhibit classical GM-CSF function. The variants, referred to herein "GM-CSF $Arg^{21}$" and "GM-CSF $Lys^{21}$" are unable to bind to high affinity receptors but are still able to fully bind the low affinity a chain of the GM-CSF receptor. Importantly, the non-glycosylated GM-CSF $Arg^{21}$ and GM-CSF $Lys^{21}$ act as antagonists, preventing the stimulatory effect of native GM-CSF. For convenience, the numbering of amino acid residues in hGM-CSF is taken from Wong et al. (1985).

By way of a shorthand notation the following three letter abbreviations for amino acid residues are used in the specification as defined in Table 1.

Where a specific amino residue is referred to by its position in the polypeptide of an HGF, the amino acid abbreviation is used with the residue number given in superscript (i.e. $Xaa^n$, wherein Xaa is the amino acid residue).

TABLE 1

| Amino acid | Three-letter abbreviation | Corresponding single-letter abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention is exemplified using GM-CSF and in particular hGM-CSF $Arg^{21}$ and hGM-CSF $Lys^{21}$. This is done, however, with the understanding that the present invention extends to all HGFs as hereinbefore described.

For example, given that there is a Glu at position 22 of IL-3 and position 13 in IL-5 which in the three dimensional structure (in the case of IL-5) occupies an equivalent position to $Glu^{21}$ of GM-CSF, then the present invention provides the basis for the creation of antagonists in IL-3 and IL-5. The substitution of Glu at these positions in IL-3 and IL-5 may be the sole mutation or it may be in combination with other amino acid mutations (including substitutions, deletions and/or additions) for the development of effective antagonists. This similarly applies to other HGFs based on the acidic or acidic-like amino acid residues in the first α-helix of the molecule. The location of the N-terminal helix can in each case be readily determined on comparable motifs from predicted helices. Such HGFs are listed in Table 2 showing the acidic or acidic-like amino acid residue in bold in the equivalent position to $Glu^{21}$ of hGM-CSF. The acidic or acidic-like amino acid residues are readily substituted by, for example, recombinant DNA technology.

According to another aspect of the present invention there is provided a modified variant including HGF comprising an amino acid sequence in the first α-helix of said HGF selected from the group consisting of:

i) His Val Asn Ala Ile Gln Xaa Ala Arg Arg Leu Leu Asn Leu (SEQ ID No. 1);

ii) Ala Leu Val Lys Xaa Thr Leu Ala Leu Leu Ser Thr His Arg Thr Leu (SEQ ID No. 2);

iii) Asn Met Ile Xaa Xaa Ile Ile Thr His Leu (SEQ ID No. 3);

iv) Leu Leu Leu Xaa Leu Gln Met Ile Leu (SEQ ID No. 4);

v) Ile Thr Leu Gln Xaa Ile Ile Lys Thr Leu (SEQ ID No. 5);

vi) Arg Tyr Ile Leu Xaa Gly Ile Ser Ala Leu Arg Lys (SEQ ID No. 6);

vii) Gly Asp Gln Tyr Xaa Ser Val Leu Met Val Ser Ile (SEQ ID No. 7);

viii) Ala Gly Ile Leu Xaa Ile Asn Phe Leu Ile Asn Lys Met Gln Glu Asp (SEQ ID No. 8);

ix) Asn Met Leu Arg Xaa Leu Arg Asp Ala Phe Ser (SEQ ID No. 9);

x) Phe Leu Leu Lys Cys Leu Xaa Gln Val Arg Lys Ile (SEQ ID No. 10); and xi) Tyr Leu Leu Glu Ala Lys Xaa Ala Glu Asn Ile Thr Thr Gly (SEQ ID No. 11);

wherein Xaa is a basic amino acid, preferably selected from the group consisting of Arg and Lys, and wherein said variant HGF is in unglycosylated form and acts as an antagonist for at least one property of the corresponding native HGF. Preferably, the haemopoietic growth factor is hGM-CSF and Xaa is Arg or Lys at position 21 of the first α-helix.

The HGF antagonists of the present invention and in particular GM-CSF $Arg^{21}$ and GM-CSF $Lys^{21}$ are useful inter alia in the treatment of myeloid and lymphocyte leukaemias, some tumours of non-haemopoietic origins and acute and chronic inflammation such as asthma and rheumatoid arthritis. These and other conditions are considered herein to result from or be facilitated by the aberrant effects of an endogenous HGF such as GM-CSF. hGM-CSF $Arg^{21}$ and hGM-CSF $Lys^{21}$ will also be useful in mobilising stem cells and progenitor cells into the circulation without the risk of activating neutrophils and monocytes. Other related molecules may have different useful properties.

The present invention, therefore, contemplates a method of treatment comprising the administration to a mammal of an effective amount of a modified HGF as hereinbefore defined and in particular hGM-CSF $Arg^{21}$ or hGM-CSF $Lys^{21}$ or both for a time and under conditions sufficient for effecting said treatment. Generally, the mammal is a human, livestock animal, companion animal or laboratory test animal. Most preferably, the mammal is a human. A single modified HGF may be administered or a combination of variants of the same HGF. For example, a range of hGM-CSF variants could be used such as a combination of hGM-CSF $Arg^{21}$ and hGM-CSF $Lys^{21}$.

TABLE 2

Cytokines related to GM-CSF exhibit a conserved acidic residue analogous to E21 in GM-CSF

| CYTOKINE[2] | HELIX[1] (Amino Acid Residue No.) | AMINO ACID SEQUENCE | SEQ ID No. |
|---|---|---|---|
| hGM-CSF | 15–28 | His Val Asn Ala Ile Gln Glu Ala Arg Arg Leu Leu Asn Leu | 12 |
| hIL-5 | 9–24 | Ala Leu Val Lys Glu Thr Leu Ala Leu Leu Ser Thr His Arg Thr Leu | 13 |
| hIL-3 | 18–27 | Asn Met Ile Asp Glu Ile Ile Thr His Leu | 14 |
| hIL-2 | 17–25 | Leu Leu Leu Aep Leu Gln Met Ile Leu | 15 |
| hIL-4 | 8–17 | Ile Thr Leu Gln Aap Ile Ile Lys Thr Leu | 16 |
| hIL-6 | 18–43 | Arg Tyr Ile Leu Aup Gly Ile Ser Ala Leu Arg Lys | 17 |
| hIL-7 | 9–20 | Gly Asp Gln Tyr Glu Ser Val Leu Met Val Ser Ile | 16 |
| hIL-9 | 7–22 | Ala Gly Ile Leu Aup Ile Asn Phe Leu Ile Asn Lys Met Gln Glu Asp | 19 |
| hIL-10 | 21–31 | Asn Met Leu Arg Aap Leu Arg ABp Ala Phe Ser | 20 |
| hG-CSF | 13–24 | Phe Leu Leu Lye Cys Leu Glu Gln Val Arg Lys Ile | 21 |
| hEPO | 4–28 | Tyr Leu Leu Glu Ala Lys Glu Ala Glu Asn Ile Thr Thr Gly | 22 |

[1]Only the pertinent portion of each helix is shown.
[2]Predicted helices are from: for IL-2, (Brandhuber et al, 1987; Zurawski and Zurawski, 1989); for hIL-3 (Parry et al, 1988); for mIL-5, (Parry et al, 1988); for hIL-6 (Bazan, 1990a); for hG-CSF, (Parry et al, 1988); for hEPO, (Bazan, 1990); for hGM-CSF the first helix was determined from the crystal structure (Karplus, 1991). The location of the N-terminal helix in the other cytokines was based on comparable motifs from these secondary structure predictions.

The present invention also provides a pharmaceutical composition comprising the variant HGFs as hereinbefore defined or combinations thereof. Most particularly, the pharmaceutical composition comprises hGM-CSF Arg$^{21}$ or hGM-CSF Lys$^{21}$ or both.

Methods for preparing pharmaceutical compositions are well known in the art and reference can conveniently be made to Remington's Pharmaceutical Sciences, Mack Publishing Company, Eaton, Pa., U.S.A. and may also include one or more pharmaceutical acceptable carriers and/or diluents.

The present invention is further described by reference to the following non-limiting Examples and/or Figures.

BRIEF DESCRIPTION OF THE DRAWINGS

FIGS. 5A, 5B and 5C is a graphical representation showing the titration of GM-CSF Arg$^{21}$ for its ability to antagonise TF-1 proliferation stimulate by either *E. coli*-derived GM-CSF (A), yeast-derived GM-CSF (B) or CHO-derived GM-CSF (C).

EXAMPLE 1

Figure 1:
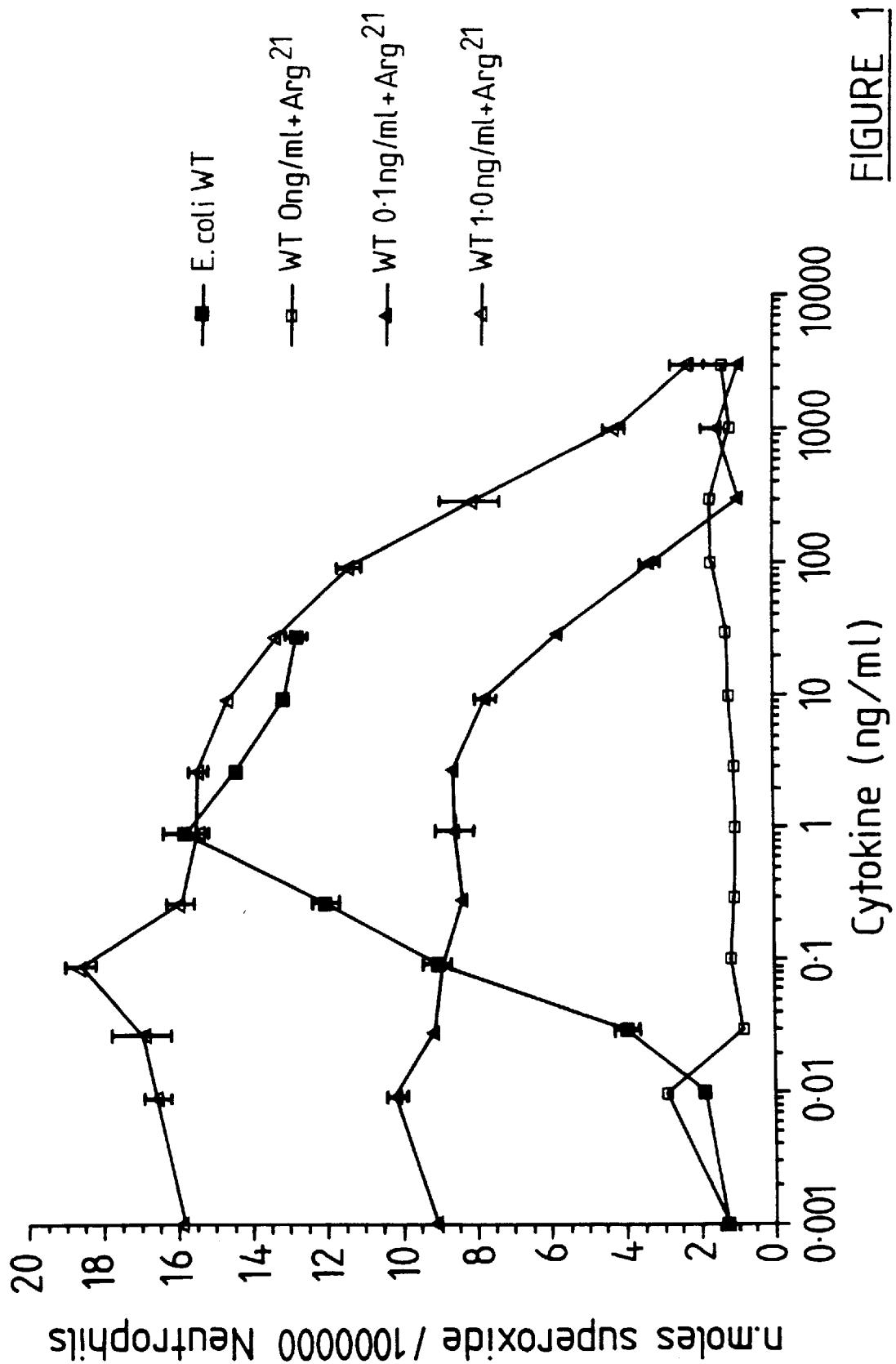
FIG. 1 is a graphical representation showing titration of *E. coli* derived GM-CSF Arg$^{21}$ for its ability to affect $O_2^-$ production in human neutrophils (□) and to antagonise the enhancement of $O_2^-$ by wild type GM-CSF tested at 1.0 ng/ml (Δ) and at 0.1 ng/ml (closed triangle).
Figure 2:
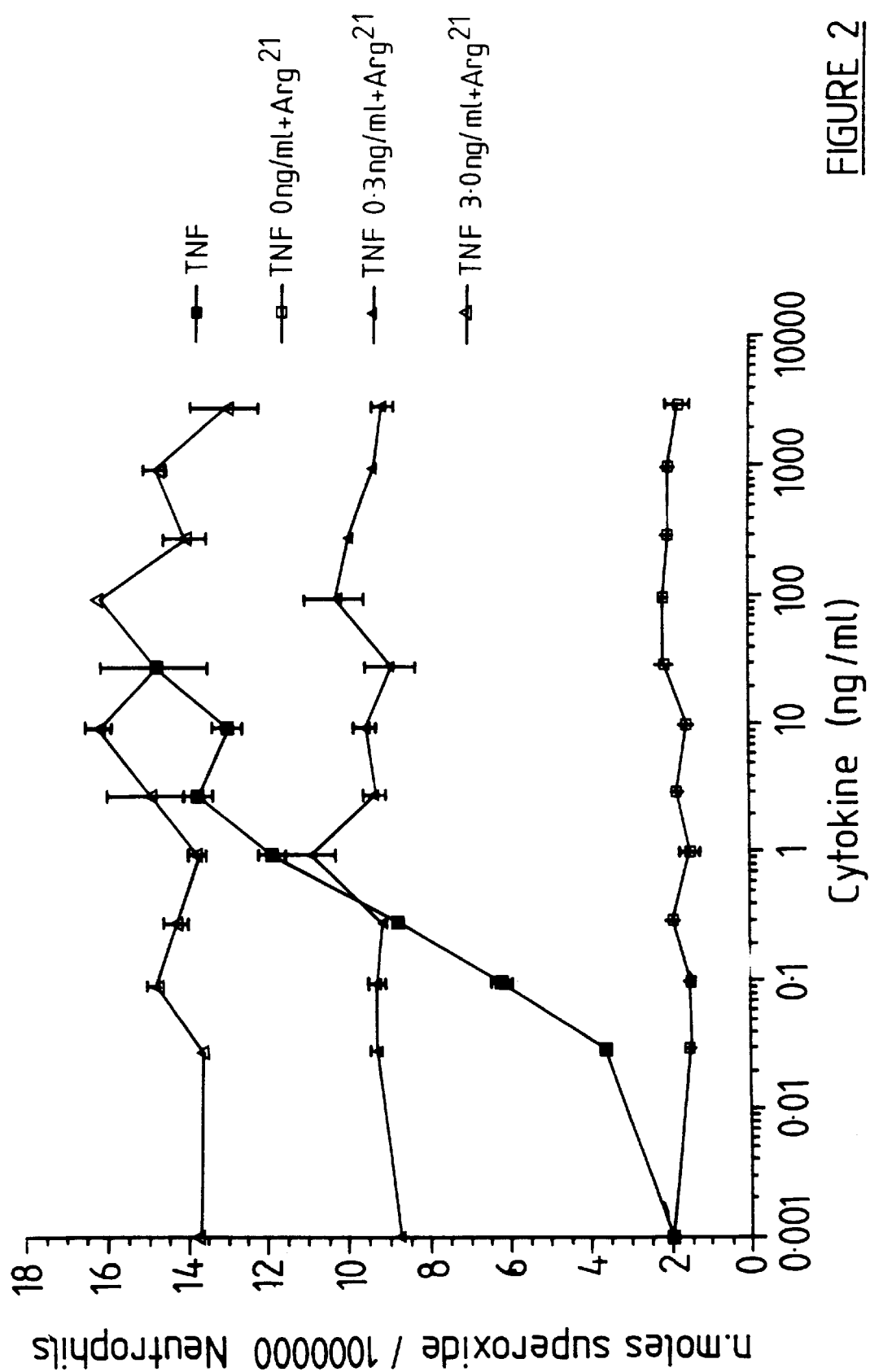
FIG. 2 is a graphical representation showing failure of *E. coli*-derived GM-CSF Arg$^{21}$ to antagonise the enhancement of $O_2^-$ production in human neutrophils stimulated with tumour necrosis factor-α (TNF-α).
Figure 3:
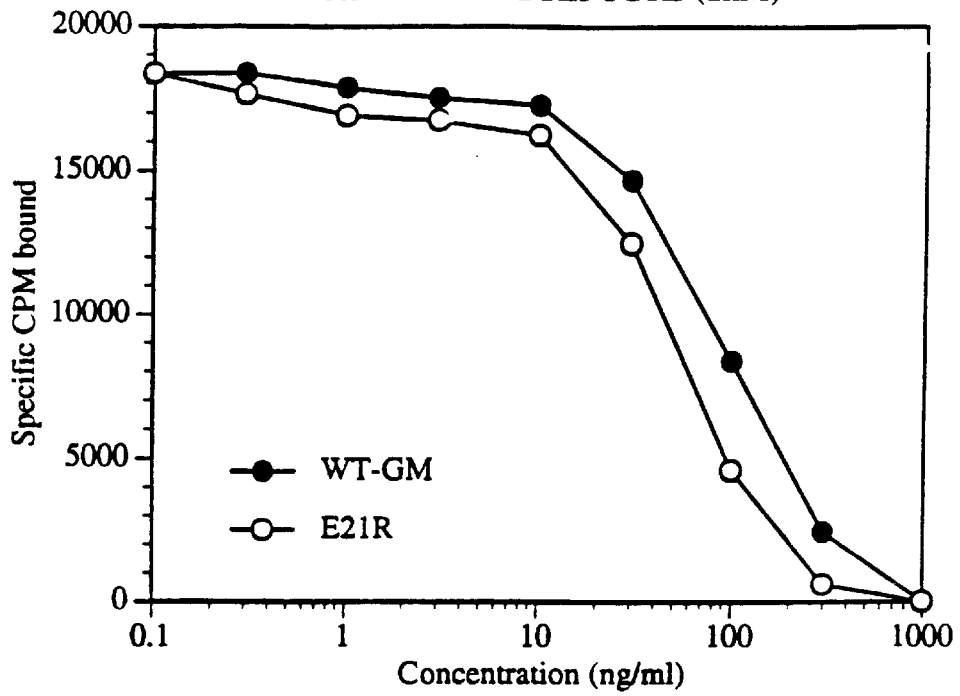
FIG. 3 is a graphical representation showing competitive inhibition of $^{125}$I-GM-CSF binding to COS cells transfected with the GM-CSF receptor a chain alone (top) or α and β chains (bottom) by GM-CSF Arg$^{21}$.
Figure 3:
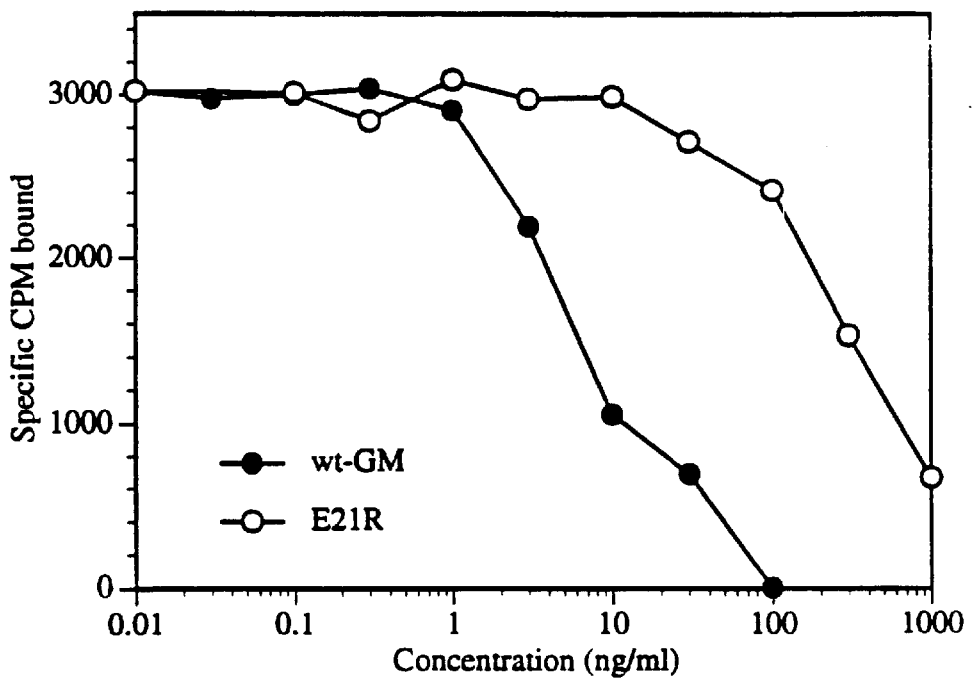
Figure 4A:
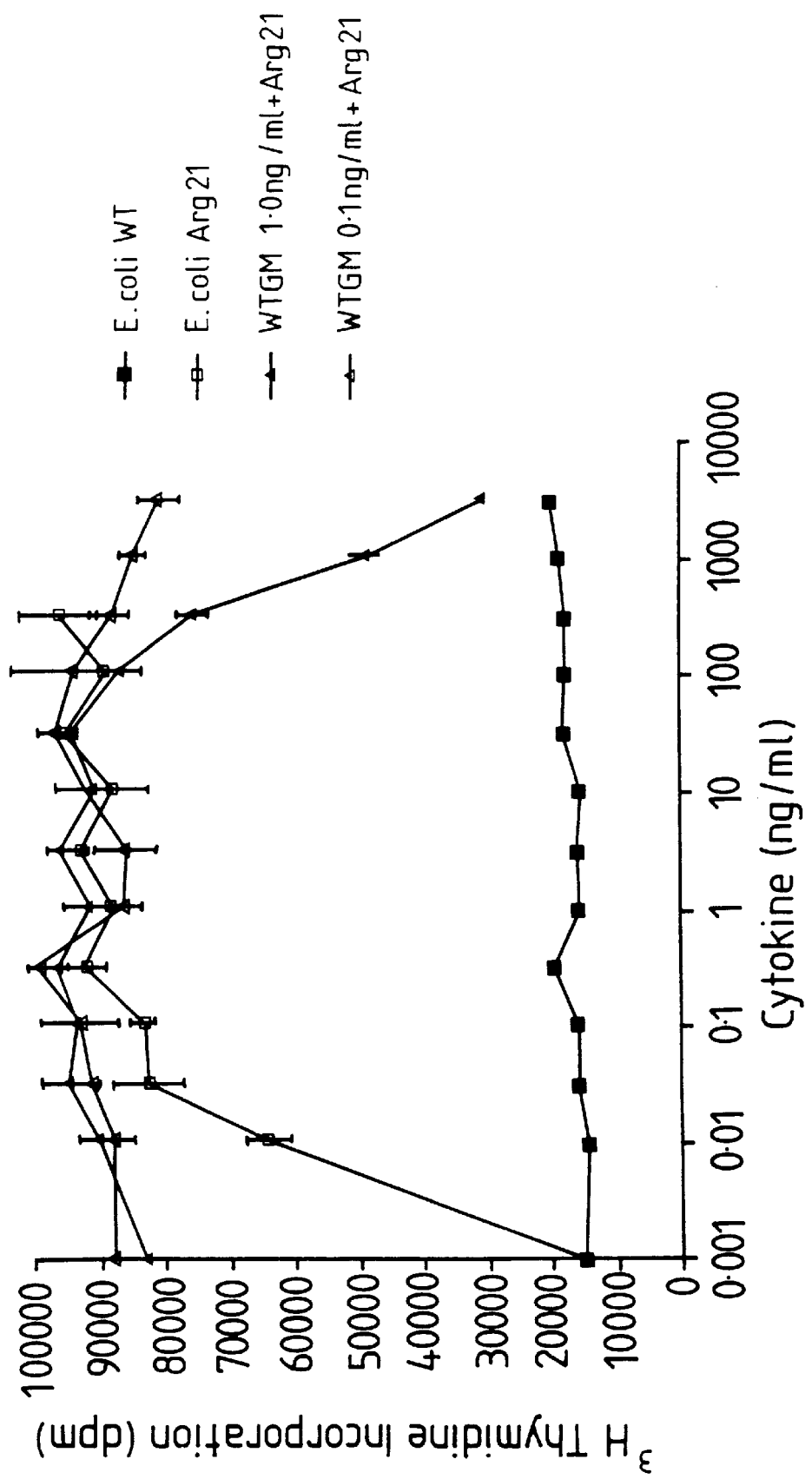
FIGS. 4A and 4B is a graphical representation showing titration of GM-CSF A g$^{21}$ for its ability to antagonise GM-CSF (A) in contrast to no effect on IL-3 (B)-mediated proliferation of TF-1 cells.
Figure 4B:
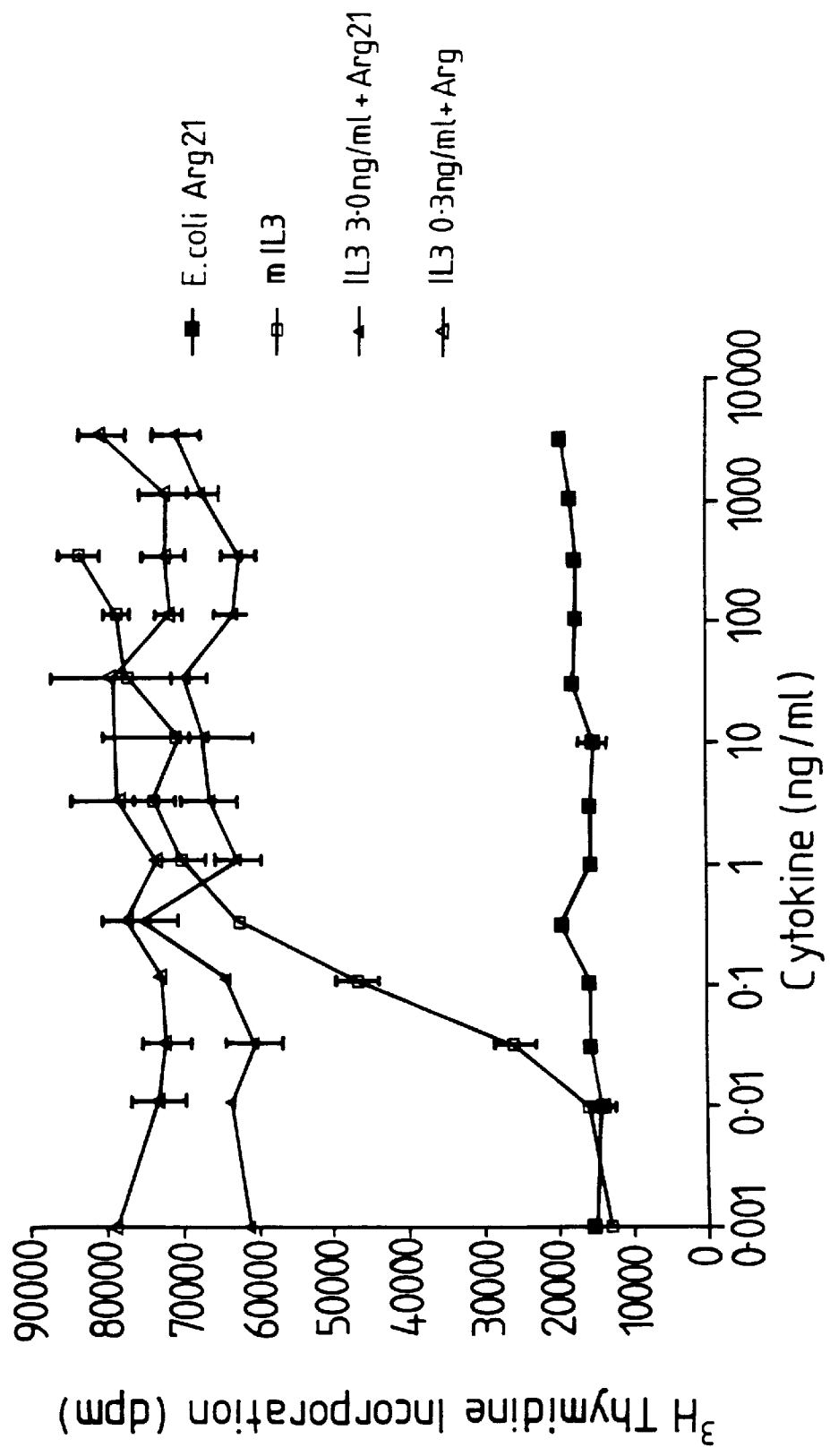

Expression of wild type and GM-CSF Arg$^{21}$ and GM-CSF Lys$^{21}$ in an *E. coli* expressed system Wild type GM-CSF was expressed in *E. coli* using a plasmid (designated pshGM-CSF) containing a synthetic human GM-CSF cDNA cloned into the *E. coli* expression vector pIN-III-OmpH3, a derivative of the vector pIN-III-OmpA2 (Ghrayeb et al, 1984). GME21R was expressed from the plasmid pSGM21.1 containing Glu$^{21}$→Arg$^{21}$ substitution and was derived from the pSGM-CSF parental plasmid. GME21K was expressed from the plasmid pSGM21.4 containing Glu$^{21}$→Lys$^{21}$ substitution and was derived from the pSGM-CSF parental plasmid.

pSGM21 was generated by initially eliminating a SacII site from the wild type GM-CSF using oligonucleotide cassette mutagenesis to generate plasmid pSGMV1. A 64 bp Nco 1/SacII fragment was then excised from the pSGMV1 plasmid and replaced by double-stranded 64 bp oligonucleotides containing the appropriate mutation in the DNA sequence. pSGM21.4 was generated by excising an 88 bp Bg11 1/SacII fragment from pSGF1 and replacing it with 88 bp oligonucleotides containing the appropriate mutation site directed mutagenesis (Zoller & Smith, 1984).

Protein was expressed in either MC1061, for wild type GM-CSF or BL21 for GME21R or GME21K, after induction by isopropyl β-D-thiogalactoside and recovered from the periplasmic space by osmotic shock (Koshland and Botstein, 1980).

GM-CSF protein was purified using a monoclonal antibody 4A21 generated in the laboratory coupled to Sepharose beads. Further purification was achieved by reversed phase HPLC using a BioRad controller and a Brownlee Aquaport C8 100×10 mm column. GM-CSF was eluted using a 30–50% gradient of acetonitrile in 0.1% trifluoroacetic acid.

Resultant purified GM-CSF was lyophilised and resuspended in 1×PBS before being quantitated by HPLC gel filtration. Samples were fractionated on a Beckman Ultrapherogel SEC3000 7.5×300 mm using a 0.1M Na Phosphate pH 7.0/01M $Na_2SO_4$ mobile phase. Purity was estimated at >95% and area under peaks corresponding to GM-CSF integrated as the extinction coefficient of 0.95 absorbance units.ml.mg$^{-1}$.

EXAMPLE 2

Visualisation of mutant GM-CSF protein

GM-CSF unpurified or purified from E. coli was size-fractionated by $NaDodSo_4$/12.5% w/v polycarylamide gel electrophoresis (Laemmli, 1970). For Western blot analysis, protein was transferred to nitrocellulose as described (Towbin et al, 1979). Filters were probed with a sheep anti-GM-CSF followed by a second layer of biotinylated-rabbit anti-sheep IgG. After a further incubation with an avidin-biotinylated-horseradish peroxidase conjugate, the complex was visualised using a diaminobenzidine substrate solution. For silver staining, the method of Morrissey (1981) was used.

EXAMPLE 3

Stimulation of haemopoietic cell proliferation

The human erythroleukaemia cell line TF-1 (and myeloid leukaemia) cells were used to measure the proliferative function of GM-CSF and GM-CSF Arg$^{21}$. Proliferation of TF-1 cells were measured by the ability to incorporate [$^3$H]-thymidine in response to increasing doses of GM-CSF. This assay was performed as described by Lopez et al (1988).

EXAMPLE 4

Functional activation of human granulocytes and monocytes

The superoxide anion production assay was carried out as previously described (Lopez et al, 1986).

EXAMPLE 5

Radioreceptor assay (a) Radioiodination of GM-CSF.

Yeast derived human GM-CSF or E. coli-derived human GM-CSF was radioiodinated by the ICl method (Contreras et al, 1983). Iodinated protein was separated from free $^{125}$I by chromatography on a Sephadex G-25 PD10 column (Pharmacia, Uppsala, Sweden), equilibrated in phosphate buffered saline (PBS) containing 0.02% w/v Tween 20, and stored at 4° C. for up to 4 weeks. Before use, the iodinated protein was purified from Tween and non-protein-associated radioactivity by cation exchange chromatography on a 0.3 ml CM-Sepharose CL-6B column (Pharmacia) and stored at 4° C. for up to 5 days. The radiolabelled GM-CSF retained >90% biological activity as judged from titration curves using non-iodinated GM-CSF as controls.

(b) Competition binding assays.

Competition for binding to high affinity and low affinity receptors used stably transfected CHO cell lines expressing either the α and β chains, or the α chain alone. The cells were suspended in binding medium consisting of RPMI-1640 supplemented with 20 mmol/l HEPES and 0.5% w/v bovine serum albumin (BSA) and 0.1% w/v sodium azide. Typically, equal volumes (50 µl) of 4×10$^4$ CHO cells, iodinated GM-CSF and different concentrations of GM-CSF and GM-CSF Arg$^{21}$ were mixed in siliconilsed glass tubes for 3 hr at 4° C. At the end of the incubation period, cell suspensions were overlaid on 0.2 ml foetal calf serum (FCS) at 4° C., centrifuged in a Beckman Microfuge 12, and the tip of each tube containing the visible cell pellet cut off and counted in a gamma counter. Specific counts were determined by first subtracting the counts, obtained in the presence of excess wild type GM-CSF.

EXAMPLE 6

Generation of hGM-CSF Variants

Figure 5B:
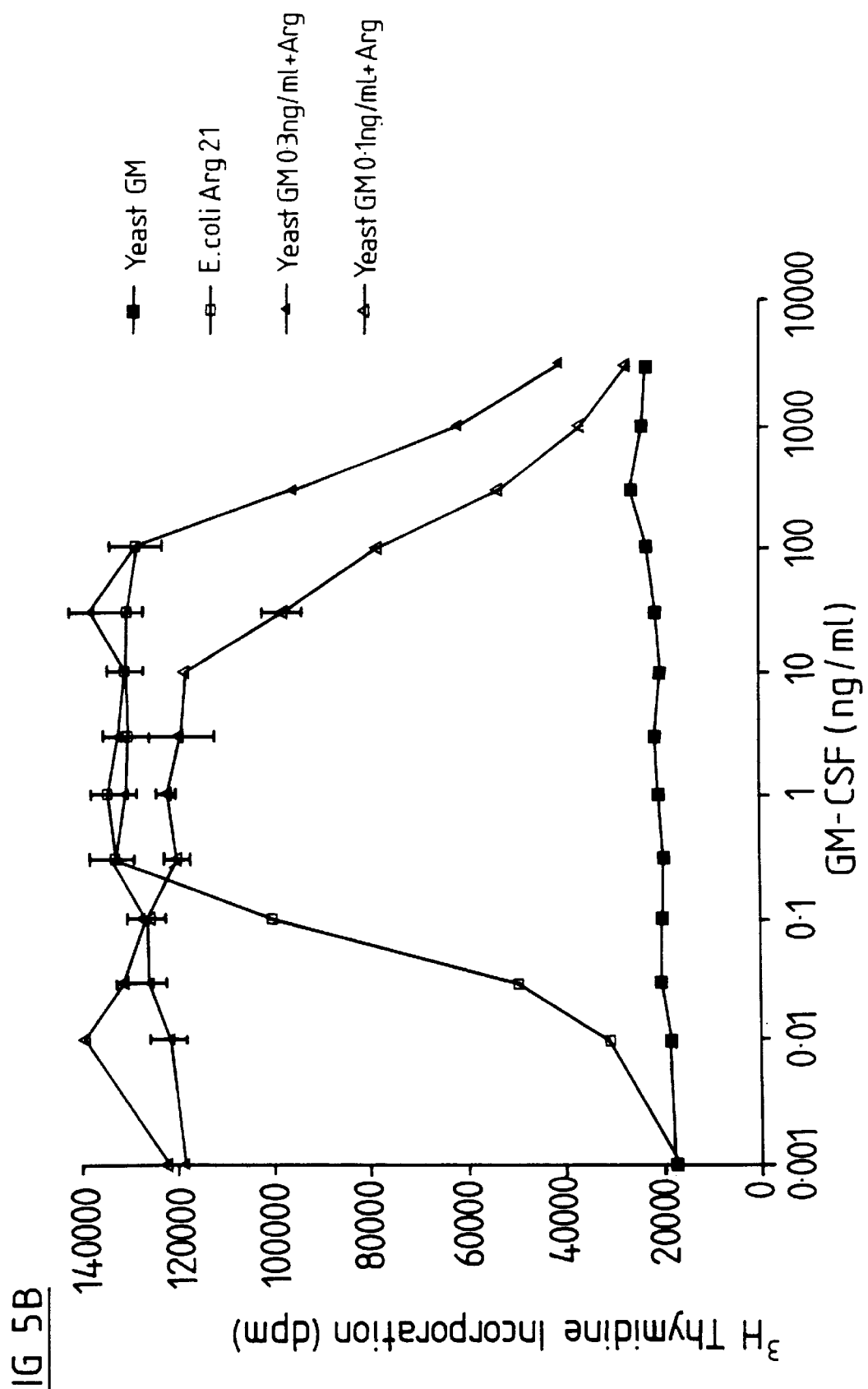
Figure 5C:
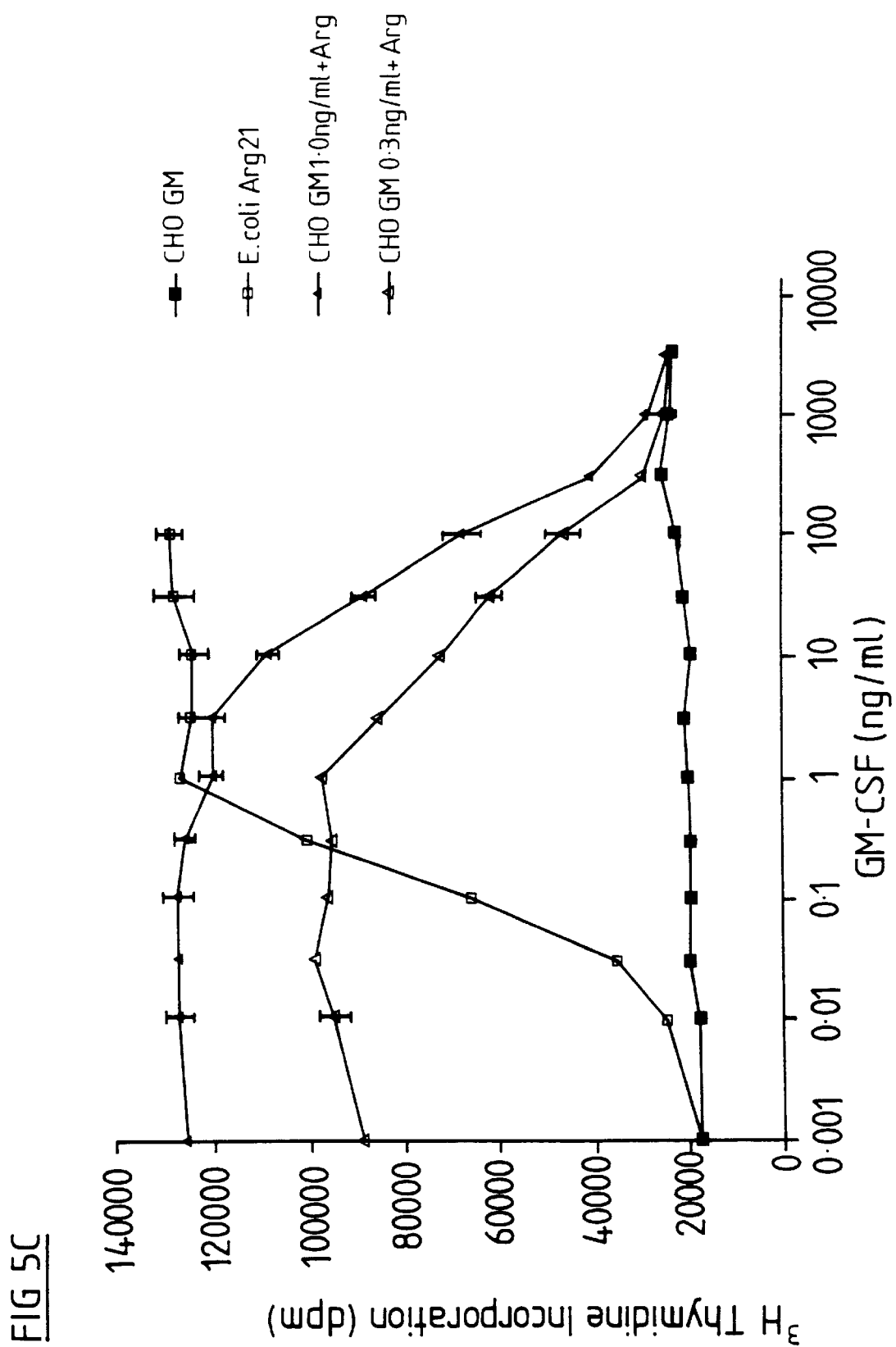

By way of example only, the generation of GM-CSF Arg$^{21}$ is hereinafter described in detail. A human GM-CSF cDNA was subjected to mutagenesis to introduce the amino acid Arg for Glu at position 21. Two mutants were obtained, one containing the $Glu^{21}$→Arg mutation and a second one containing a double mutation $X^{10}$→Ile and $Glu^{21}$→Arg. These mutants were cloned into the expression system piN OMPIII and expressed in *E. coli*. Wild type (WT) GM-CSF was expressed in MC1061. GM-CSF $Arg^{21}$ could not be expressed in MC1061. Of twenty strains tested for GM-CSF $Arg^{21}$ expression, BL21 was the highest producer and used for subsequent studies.

To obtain purified GM-CSF $Arg^{21}$ in high yields a two-step purification procedure was devised. In the first step, GM-CSF $Arg^{21}$ was purified by an affinity column constructed with a monoclonal antibody (4A12) that binds to GM-CSF in solution and with high affinity. Affinity-purified GM-CSF $Arg^{21}$ was then purified by reverse-phase HPLC and quantitated by HPLC before being analysed for biological and binding activities.

It was found that *E. coli*-derived GM-CSF $Arg^{21}$ was unable to enhance neutrophil $O_{2-}$ production up to a concentration of 3,000 ng/ml (FIG. 1). This is different to the inventors' previous results with CHO-derived (i.e. glycosylated) GM-CSF $Arg^{21}$ which was able to enhance neutrophil function at approximately 30 ng/ml which represents a 300 fold reduced potency compared to wild type GM-CSF (Lopez et al, 1992).

Despite its inability to activate neutrophils, *E. coli*-derived GM-CSF $Arg^{21}$ was able to bind as well as wild type GM-CSF to the α-chain of the GM-CSF receptor (FIG. 3). In contrast, GM-CSF $Arg^{21}$ exhibited an approximate 100-fold reduction in binding to the αβ GM-CSF receptor complex (FIG. 3) indicating that the influence of the β chain has been selectively lost.

This is the first time that a GM-CSF mutant is shown to have unaltered binding to the GM-CSF receptor α-chain as well as being devoid of agonistic activity. This indicates that whilst binding to the α chain is necessary for GM-CSF activity it is not sufficient, and that GM-CSF binding to the β chain is required for GM-CSF-mediated activation.

Since *E. coli*-derived GM-CSF $Arg^{21}$ was not able to stimulate neutrophils yet filly bound the GM-CSF receptor α chain, it was tested for antagonistic activity. The inventors found that this mutant fully inhibited the effect of wild type GM-CSF with an approximately 300-fold excess required to induce 50% inhibition of *E. coli*-derived wild type GM-CSF (FIG. 1). This antagonistic effect was specific for GM-CSF as judged by the lack of antagonistic effect of GM-CSF $Arg^{21}$ on TNF enhancement of neutrophil $O_2^-$ production (FIG. 2).

The antagonistic effect of *E. coli*-derived GM-CSF $Arg^{21}$ was present whether wild type GM-CSF was expressed in *E. coli* (FIG. 5A), yeast (FIG. 5B) or CHO cells (FIG. 5C). In keeping with the differences in binding affinity between heavily glycosylated CHO GM-CSF (lower affinity), partially glycosylated yeast GM-CSF (intermediate affinity)

and unglycosylated *E. coli* GM-CSF (higher affinity), *E. coli*-derived GM-CSF $Arg^{21}$ antagonised better the CHO wild type GM-CSF (FIGS. 5A, 5B, and 5C).

Figure 6A:
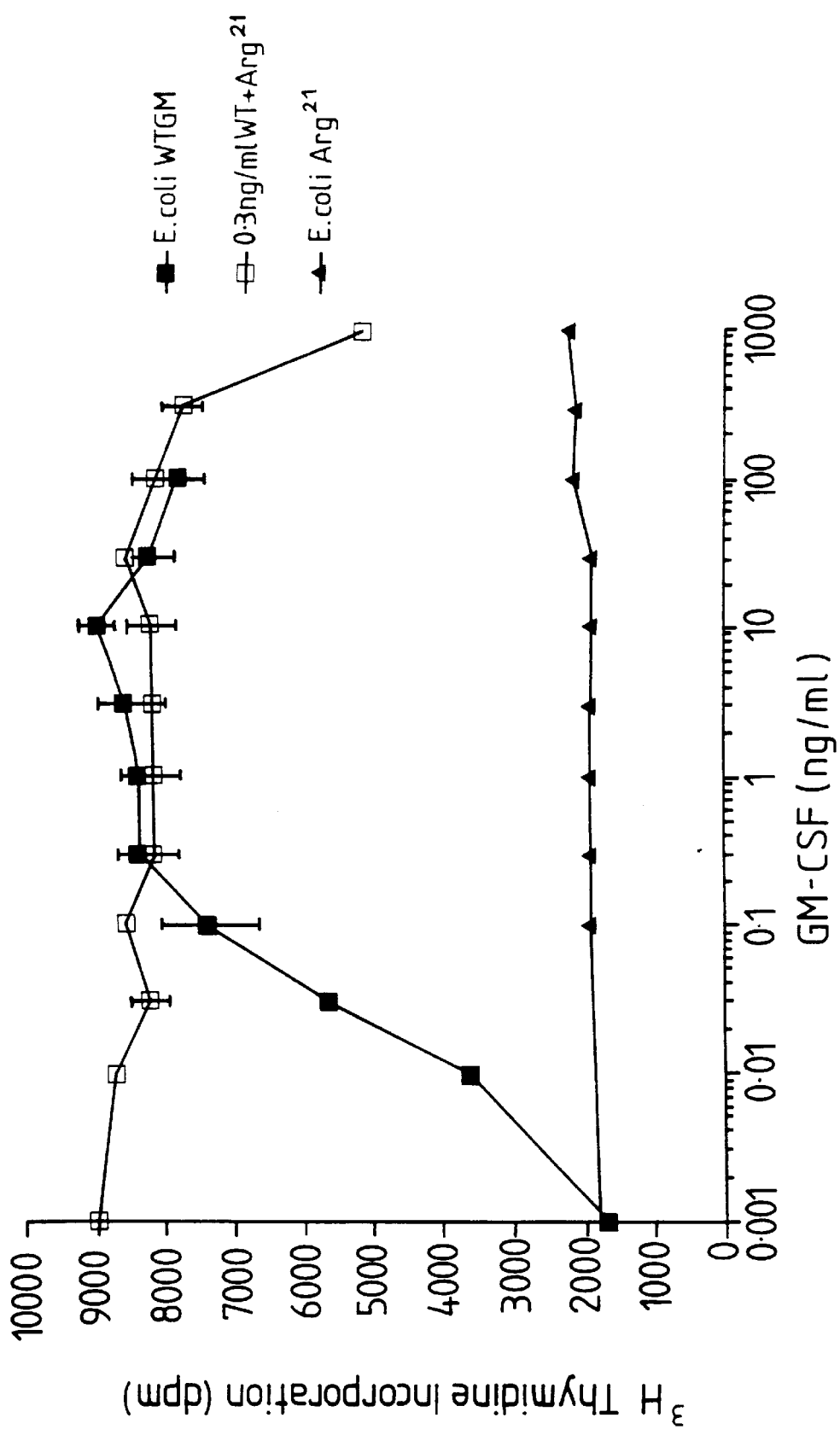
FIGS. 6A, 6B and 6C is a graphical representation showing the titration of GM-CSF Arg$^{21}$ for its ability to antagonise three primary human myeloid leukaemia (A, B & C) ex vivo.
Figure 6B:
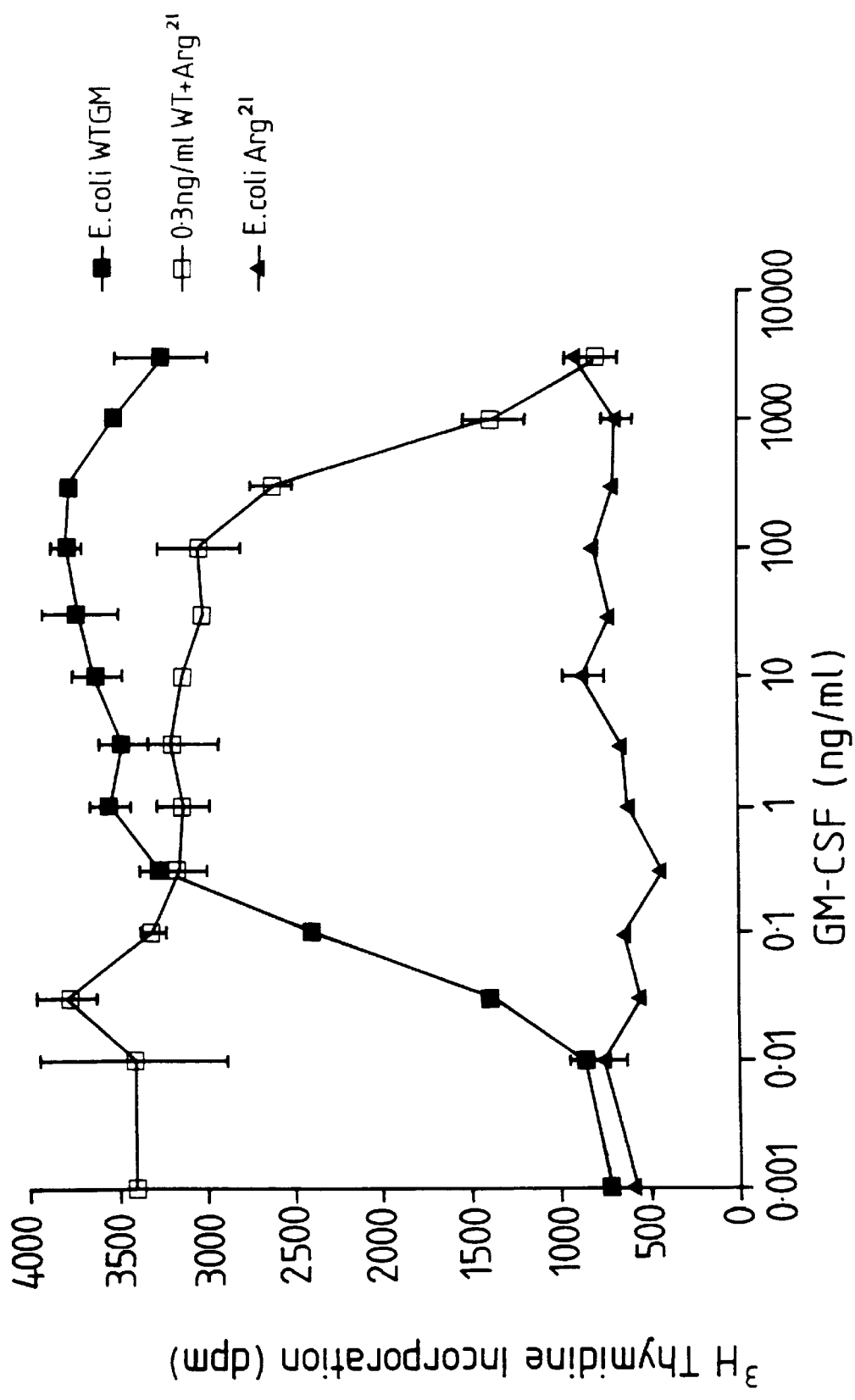
Figure 6C:
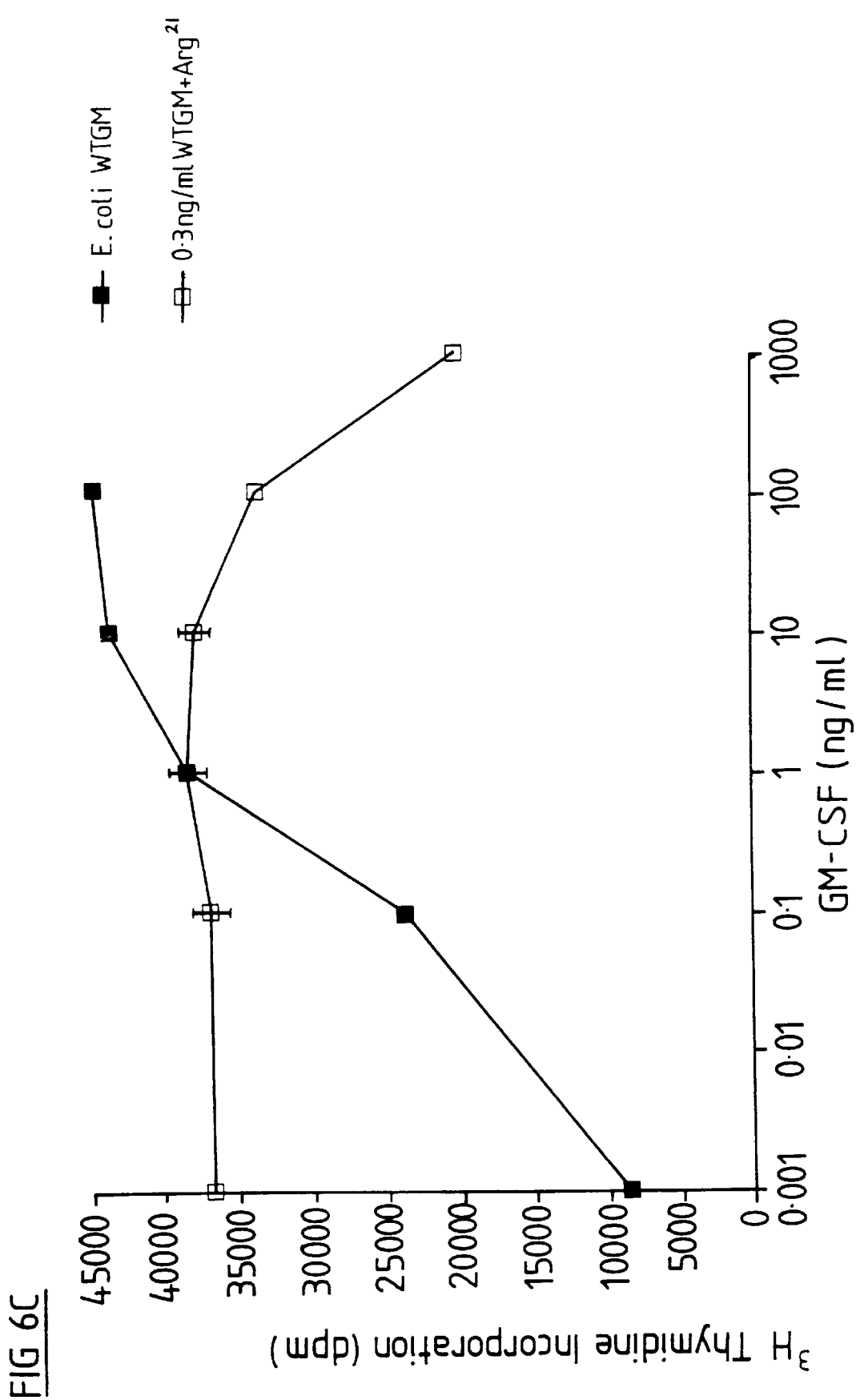
Figure 7A:
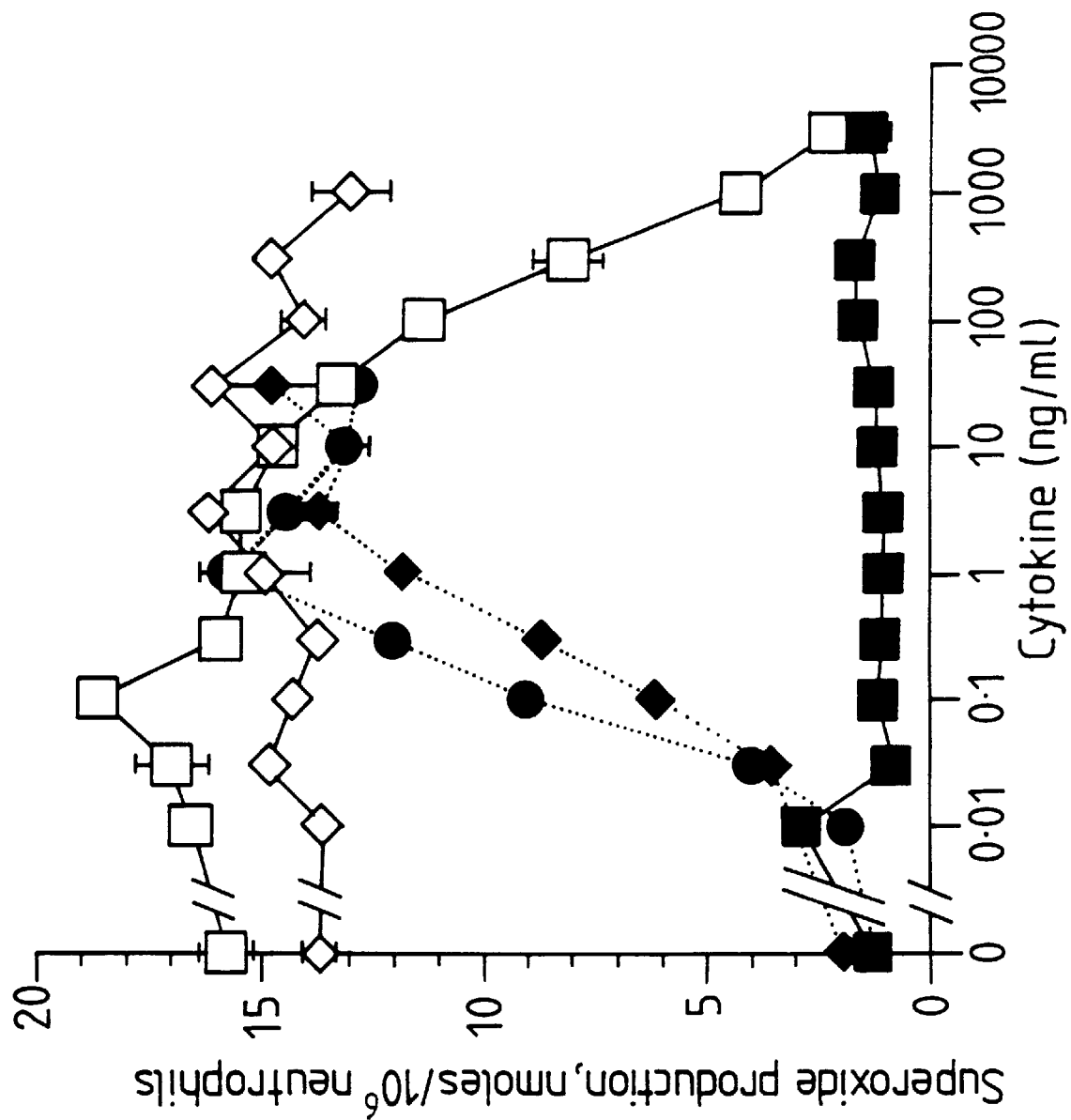
FIGS. 7A and 7B is a graphical representation showing that E21R antagonises both GM-CSF but not TNF-α-mediated stimulation of human neutrophils (A), and both E21R and E21K also antagonise neurtrophil stimulation by CHO cell-derived GM-CSF (B). In panel A, titrations of *E. coli*-derived wild type GM-CSF (●), TNF-α (◆) and E21R (■) are shown. In antagonistic experiments, E21R was titrated against 1 ng/ml of *E. coli*-derived GM-CSF (□) or 3 ng/ml TNF-α (◇). In panel B, titrations of CHO cell-derived wild type GM-CSF (○), E21R (■) and E21K (▲) are shown. In antagonistic experiments, E21R (□) or E21K (△) were titrated against 3 ng/ml CHO cell-derived GM-CSF. Each value represents the mean of triplicate determinations and error bars represent the SEM.
Figure 7B:
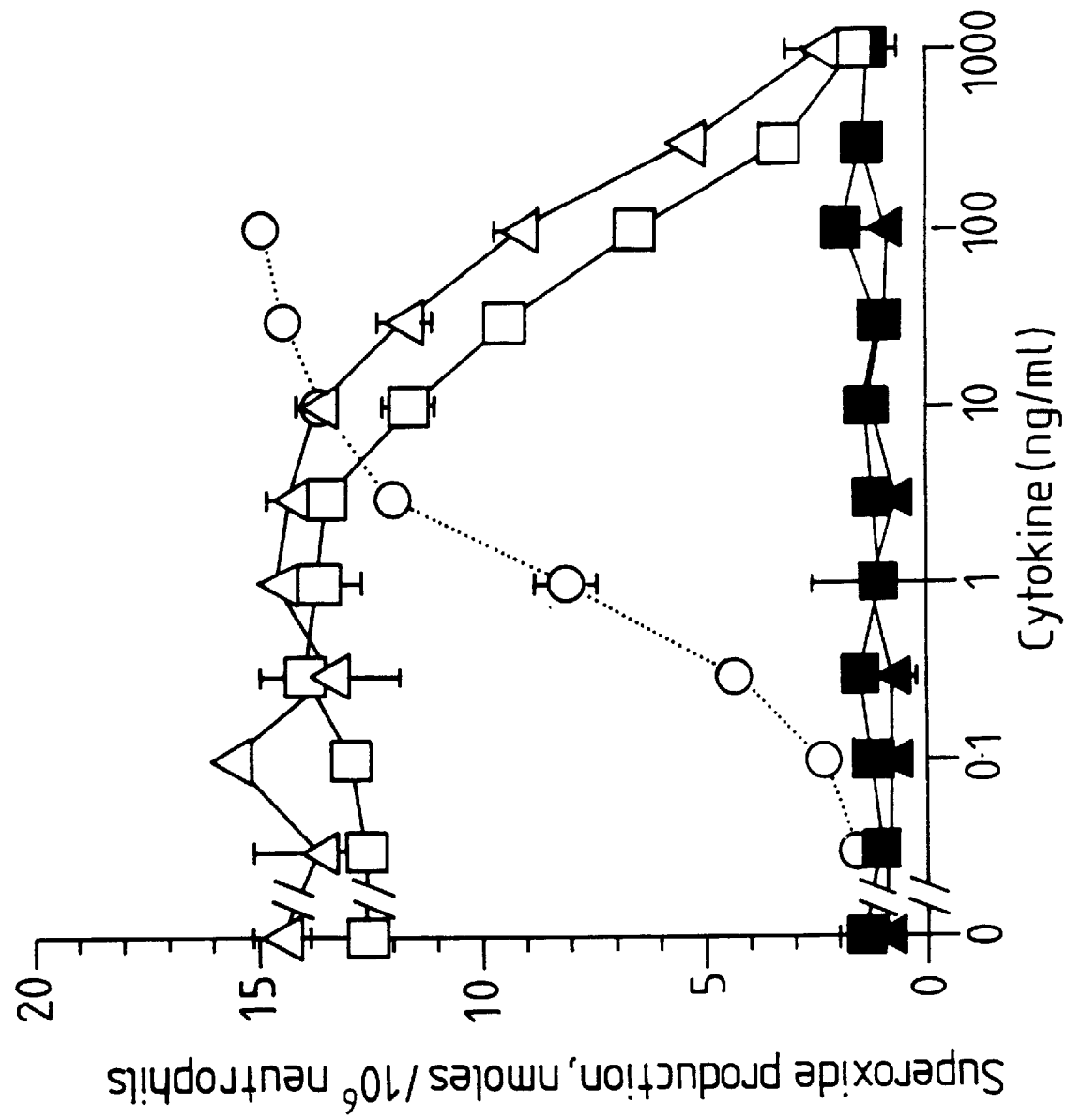

The antagonism of *E. coli*-derived GM-CSF $Arg^{21}$ was not restricted to proliferation of the established TF-1 cell line but was also seen in primary myeloid leukaemias. In three different leukaemias, *E. coli*-derived GM-CSF $Arg^{21}$ antagonised the proliferative effect of wild type *E. coli* GM-CSF with an $EC_{50}$ that varied with each leukaemia (FIG. 6A, 6B and 6C). These results show that an unglycosylated GM-CSF molecule with a mutated Glu for an Arg in position 21 of the first α-helix is able to antagonise native GM-CSF.

Since the mutated Glu in GM-CSF is in a position where the same acidic residue or similar acidic residues (e.g. Asp) are present in related growth factors (see Table 2), this invention extends to antagonistic molecules for these growth factors constructed by incorporating the analogous charge reversal mutation. In particular, given that the GM-CSF, IL-3 and IL-5 receptor share the β chain, the $Glu^{22}$ in IL-3 and the $Glu^{13}$ in IL-5 are predicted to play a similar role. Other variant HGFs are shown in Examples 3 to 22 in which the equivalent or similar amino acid residue to $Glu^{21}$ of hGM-CSF is replaced by either Arg or Lys. In these Examples, the amino acid sequences are provided for the relevant portion of the first α-helix carrying the substitution (see Table 2).

EXAMPLE 7 hGM-CSF $Lys^{21}$

His Val Asn Ala Ile Gln Lys Ala Arg Arg Leu Leu Asn Leu (SEQ ID NO. 23)

EXAMPLE 8 hIL-5 $Lys^{13}$

Ala Leu Val Lys Lys Thr Leu Ala Leu Leu Ser Thr His Arg Thr Leu (SEQ ID NO. 24)

EXAMPLE 9 hIL-5 $Arg^{13}$

Ala Leu Val Lys Arg Thr Leu Ala Leu Leu Ser Thr His Arg Thr Leu (SEQ ID NO. 25)

EXAMPLE 10 hIL-3 Variants

| | |
|---|---|
| Asn Met Ile Asp Lys Ile Ile Thr His Leu | hIL-3 $Lys^{22}$ (SEQ ID NO. 26) |
| Asn Met Ile Lys Glu Ile Ile Thr His Leu | hIL-3 $Lys^{21}$ (SEQ ID NO. 27) |
| Asn Met Ile Asp Arg Ile Ile Thr His Leu | hIL-3 $Arg^{22}$ (SEQ ID NO. 28) |
| Asn Met Ile Arg Glu Ile Ile Thr His Leu | hIL-3 $Arg^{21}$ (SEQ ID NO. 29) |
| Asn Met Ile Lys Lys Ile Ile Thr His Leu | hIL-3 $Lys^{21}$ $Lys^{22}$ (SEQ ID NO. 30) |
| Asn Met Ile Arg Arg Ile Ile Thr His Leu | hIL-3 $Arg^{21}$ $Arg^{22}$ (SEQ ID NO. 31) |

EXAMPLE 11 hIL-2 $Lys^{20}$

Leu Leu Leu Lys Leu Gln Met Ile Leu (SEQ ID NO. 32)

EXAMPLE 12 hIL-2 $Arg^{20}$

Leu Leu Leu Arg Leu Gln Met Ile Leu (SEQ ID NO. 33)

EXAMPLE 13 hIL-4 $Lys^{12}$

Ile Thr Leu Gin Lys Ile Ile Lys Thr Leu (SEQ ID NO. 34)

EXAMPLE 14 hIL-4 $Arg^{12}$

Ile Thr Leu Gln Arg Ile Ile Lys Thr Leu (SEQ ID NO. 35)

EXAMPLE 15 hIL-6 $Lys^{22}$

Arg Tyr Ile Leu Lys Gly Ile Ser Ala Leu Arg Lys (SEQ ID NO. 36)

EXAMPLE 16 hIL-6 $Arg^{22}$

Arg Tyr Ile Leu Arg Gly Ile Ser Ala Leu Arg Lys (SEQ ID NO. 37)

EXAMPLE 17 hIL-7 $Lys^{13}$

Gly Asp Gln Tyr Lys Ser Val Leu Met Val Ser Ile (SEQ ID NO. 38)

EXAMPLE 18 hIL-7 $Arg^{13}$

Gly Asp Gin Tyr Arg Ser Val Leu Met Val Ser Ile (SEQ ID NO. 39)

EXAMPLE 19 hIL-9 $Lys^{11}$

Ala Gly Ile Leu Lys Ile Asn Phe Leu Ile Asn Lys Met Gln Glu Asp (SEQ ID NO. 40)

EXAMPLE 20 hIL-9 $Arg^{11}$

Ala Gly Ile Leu Arg Ile Asn Phe Leu Ile Asn Lys Met Gin Glu Asp (SEQ ID NO. 41)

EXAMPLE 21 hIL-10 $Lys^{25}$

Asn Met Leu Arg Lys Leu Arg Asp Ala Phe Ser (SEQ ID NO. 42)

EXAMPLE 22 hIL-10 $Arg^{25}$

Asn Met Leu Arg Arg Leu Arg Asp Ala Phe Ser (SEQ ID NO. 43)

EXAMPLE 23 hG-CSF $Lys^{19}$

Phe Leu Leu Lys Cys Leu Lys Gln Val Arg Lys Ile (SEQ ID NO. 44)

EXAMPLE 24 hG-CSF Arg[19]

Phe Leu Leu Lys Cys Leu Arg Gin Val Arg Lys Ile (SEQ ID NO. 45)

EXAMPLE 25 hEPO Lys[10]

Tyr Leu Leu Glu Ala Lys Lys Ala Glu Asn Ile Thr Thr Gly (SEQ ID NO. 46)

EXAMPLE 26 hEPO Arg[10]

Tyr Leu Leu Glu Ala Lys Arg Ala Glu Asn Ile Thr Thr Gly (SEQ ID NO. 47)

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Bazan J. F. (1990) *Immunol Today* 11, 350–354.
Brandhuber B. J. et al. (1987) *Science* 238, 1707–1709.
Contreras M. A. et al. (1983) *Methods Enzymol* 92, 277–292.
Diederich et al. (1991) *Science* 254, 1779–1782.
Elliott M. J. et al. (1990) *J Immunol* 145, 167–176.
Gasson J. C. et al. (1986) *Proc Natl Acad Sci USA* 83, 669–673.
Gearing D. P. et al. (1989) *EMBO J* 8, 3667–3676.
Ghrayeb J. et al. (1984) *EMBO J* 3, 2437–2442.
Goodall G. J. et al. (1993) *Growth Factors* 8, 87–97.
Hayashide K. et al. (1990) *Proc Natl Acad Sci USA* 87, 9655–9659.
Koshland D. and Botstein D. (1980) *Cell* 20, 749–760.
Laemmnli U. K. (1970) *Nature* 227, 680–685.
Lopez A. F. et al. (1986) *J Clin Invest* 78, 1202–1228.
Lopez A. F. et al. (1988) *Blood* 72, 1797–1804.
Lopez A. F. et al. (1992) *EMBO J* 11, 909–916.
Morrisey J. H. (1981) *Anal Biochem* 117, 307–310.
Parry, D. A. D. et al. (1988) *J Mol Recogn* 1, 107–110.
Towbin H. et al. (1979) *Proc Natl Acad Sci USA* 76, 4350–4354.
Wong G. et al. (1985) *Science* 228, 810–815.
Zoller M. J. and Smith M. (1984) *DNA* 3, 479–488.
Zurawski S. M. and Zurawski G. (1989) *EMBO J* 8, 2583–2590.

---

```
SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
        (A) LENGTH: 14 amino
acid residues
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:1:

His Val Asn Ala Ile Gln Xaa Ala Arg Arg Le
u Leu Asn Leu
1               5
                10

(2) INFORMATION FOR SEQ ID NO:2:

(i) SEQUENCE CHARACTERISTICS:
        (A) LENGTH: 16 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:2:

Ala Leu Val Lys Xaa Thr Leu Ala Leu Leu Se
r Thr His Arg Thr Leu
1               5
                10
                15
```

(2) INFORMATION FOR SEQ ID NO:3:

(i) SEQUENCE CHARACTERISTICS:
        (A) LENGTH: 10 amino acid residues
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:3:

```
Asn Met Ile Xaa Xaa Ile Ile Thr His Leu
1               5                   10
```

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:4:

```
Leu Leu Leu Xaa Leu Gln Met Ile Leu
1               5
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:5:

```
Ile Thr Leu Gln Xaa Ile Ile Lys Thr Leu
1               5                   10
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:6:

```
Arg Tyr Ile Leu Xaa Gly Ile Ser Ala Leu Arg Lys
1               5                   10
```

(2) INFORMATION FOR SEQ ID NO:7:

(i) SEQUENCE CHARACTERISTICS:
        (A) LENGTH: 12 amino acids
        (B) TYPE: amino acid

```
        (C) STRANDEDNESS: single
        (D) TOPOLOGY: linear (ii) MOLECULE TYPE: polypeptide (xi) SEQUENCE DESCRIPTION: SEQ ID NO:7:

Gly Asp Gln Tyr Xaa Ser Val Leu Met Val Se
r Ile
1               5
                    10

(2) INFORMATION FOR SEQ ID NO:8:

(i) SEQUENCE CHARACTERISTICS:
        (A) LENGTH: 16 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:8:

Ala Gly Ile Leu Xaa Ile Asn Phe Leu Ile As
n Lys Met Gln Glu Asp
1               5
                    10
                        15

(2) INFORMATION FOR SEQ ID NO:9:

(i) SEQUENCE CHARACTERISTICS:
        (A) LENGTH: 11 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:9:

Asn Met Leu Arg Xaa Leu Arg Asp Ala Phe Se
r
1               5
                    10

(2) INFORMATION FOR SEQ ID NO:10:

(i) SEQUENCE CHARACTERISTICS:
        (A) LENGTH: 12 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:10:

Phe Leu Leu Lys Cys Leu Xaa Gln Val Arg Ly
s Ile
1               5
                    10

(2) INFORMATION FOR SEQ ID NO:11:

(i) SEQUENCE CHARACTERISTICS:
        (A) LENGTH: 14 amino
acids
        (B) TYPE: amino acid
        (C) STRANDEDNESS: single
        (D) TOPOLOGY: linear
```

(ii) MOLECULE TYPE: polypeptide (xi) SEQUENCE DESCRIPTION: SEQ ID NO:11:

Tyr Leu Leu Glu Ala Lys Xaa Ala Glu Asn Il
e Thr Thr Gly
1               5
                    10

(2) INFORMATION FOR SEQ ID NO:12:

(i) SEQUENCE CHARACTERISTICS:
        (A) LENGTH: 14 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:12:

His Val Asn Ala Ile Gln Glu Ala Arg Arg Le
u Leu Asn Leu
1               5
                    10

(2) INFORMATION FOR SEQ ID NO:13:

(i) SEQUENCE CHARACTERISTICS:
        (A) LENGTH: 16 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:13:

Ala Leu Val Lys Glu Thr Leu Ala Leu Leu Se
r Thr His Arg Thr Leu
1               5
                    10
                        15

(2) INFORMATION FOR SEQ ID NO:14:

(i) SEQUENCE CHARACTERISTICS:
        (A) LENGTH: 10 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:14:

Asn Met Ile Asp Glu Ile Ile Thr His Leu
1               5
                    10

(2) INFORMATION FOR SEQ ID NO:15:

(i) SEQUENCE CHARACTERISTICS:
        (A) LENGTH: 9 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:15:

```
Leu Leu Leu Asp Leu Gln Met Ile Leu
1               5
```

(2) INFORMATION FOR SEQ ID NO:16:

(i) SEQUENCE CHARACTERISTICS:
　　　　　　(A) LENGTH: 10 amino
acids
　　　　　　(B) TYPE: amino acid
　　　　　　(C) STRANDEDNESS: single
　　　　　　(D) TOPOLOGY: linear (ii) MOLECULE TYPE: polypeptide (xi) SEQUENCE DESCRIPTION: SEQ ID NO:16:

```
Ile Thr Leu Gln Asp Ile Ile Lys Thr Leu
1               5
                        10
```

(2) INFORMATION FOR SEQ ID NO:17:

(i) SEQUENCE CHARACTERISTICS:
　　　　　　(A) LENGTH: 12 amino
acids
　　　　　　(B) TYPE: amino acid
　　　　　　(C) STRANDEDNESS: single
　　　　　　(D) TOPOLOGY: linear (ii) MOLECULE TYPE: polypeptide (xi) SEQUENCE DESCRIPTION: SEQ ID NO:17:

```
Arg Tyr Ile Leu Asp Gly Ile Ser Ala Leu Ar
g Lys
1               5
                        10
```

(2) INFORMATION FOR SEQ ID NO:18:

(i) SEQUENCE CHARACTERISTICS:
　　　　　　(A) LENGTH: 12 amino
acids
　　　　　　(B) TYPE: amino acid
　　　　　　(C) STRANDEDNESS: single
　　　　　　(D) TOPOLOGY: linear (ii) MOLECULE TYPE: polypeptide (xi) SEQUENCE DESCRIPTION: SEQ ID NO:18:

```
Gly Asp Gln Tyr Glu Ser Val Leu Met Val Se
r Ile
1               5
                        10
```

(2) INFORMATION FOR SEQ ID NO:19:

(i) SEQUENCE CHARACTERISTICS:
　　　　　　(A) LENGTH: 16 amino
acids
　　　　　　(B) TYPE: amino acid
　　　　　　(C) STRANDEDNESS: single
　　　　　　(D) TOPOLOGY: linear (ii) MOLECULE TYPE: polypeptide (xi) SEQUENCE DESCRIPTION: SEQ ID NO:19:

```
Ala Gly Ile Leu Asp Ile Asn Phe Leu Ile As
n Lys Met Gln Glu Asp
1               5
                        10
                                15
```

-continued (2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:20:

```
Asn Met Leu Arg Asp Leu Arg Asp Ala Phe Ser
1               5                  10
```

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:21:

```
Phe Leu Leu Lys Cys Leu Glu Gln Val Arg Lys Ile
1               5                  10
```

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:22:

```
Tyr Leu Leu Glu Ala Lys Glu Ala Glu Asn Ile Thr Thr Gly
1               5                  10
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:23:

```
His Val Asn Ala Ile Gln Lys Ala Arg Arg Leu Leu Asn Leu
1               5                  10
```

(2) INFORMATION FOR SEQ ID NO:24:

(i) SEQUENCE CHARACTERISTICS:
        (A) LENGTH: 16 amino acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:24:

Ala Leu Val Lys Lys Thr Leu Ala Leu Leu Se
r Thr His Arg Thr Leu
1               5
                        10
                        15

(2) INFORMATION FOR SEQ ID NO:25:

(i) SEQUENCE CHARACTERISTICS:
            (A) LENGTH: 16 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:25:

Ala Leu Val Lys Arg Thr Leu Ala Leu Leu Se
r Thr His Arg Thr Leu
1               5
                        10
                        15

(2) INFORMATION FOR SEQ ID NO:26:

(i) SEQUENCE CHARACTERISTICS:
            (A) LENGTH: 10 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:26:

Asn Met Ile Asp Lys Ile Ile Thr His Leu
1               5
                        10

(2) INFORMATION FOR SEQ ID NO:27:

(i) SEQUENCE CHARACTERISTICS:
            (A) LENGTH: 10 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:27:

Asn Met Ile Lys Glu Ile Ile Thr His Leu
1               5
                        10

(2) INFORMATION FOR SEQ ID NO:28:

(i) SEQUENCE CHARACTERISTICS:
            (A) LENGTH: 10 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:28:

Asn Met Ile Asp Arg Ile Ile Thr His Leu
1               5                   10

(2) INFORMATION FOR SEQ ID NO:29:

(i) SEQUENCE CHARACTERISTICS:
        (A) LENGTH: 10 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:29:

Asn Met Ile Arg Glu Ile Ile Thr His Leu
1               5                   10

(2) INFORMATION FOR SEQ ID NO:30:

(i) SEQUENCE CHARACTERISTICS:
        (A) LENGTH: 10 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:30:

Asn Met Ile Lys Lys Ile Ile Thr His Leu
1               5                   10

(2) INFORMATION FOR SEQ ID NO:31:

(i) SEQUENCE CHARACTERISTICS:
        (A) LENGTH: 10 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:31:

Asn Met Ile Arg Arg Ile Ile Thr His Leu
1               5                   10

(2) INFORMATION FOR SEQ ID NO:32:

(i) SEQUENCE CHARACTERISTICS:
        (A) LENGTH: 9 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:32:

Leu Leu Leu Lys Leu Gln Met Ile Leu
1               5

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:33:

Leu Leu Leu Arg Leu Gln Met Ile Leu
1               5

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:34:

Ile Thr Leu Gln Lys Ile Ile Lys Thr Leu
1               5
                  10

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:35:

Ile Thr Leu Gln Arg Ile Ile Lys Thr Leu
1               5
                  10

(2) INFORMATION FOR SEQ ID NO:36:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:36:

Arg Tyr Ile Leu Lys Gly Ile Ser Ala Leu Arg Lys
1               5
                  10

(2) INFORMATION FOR SEQ ID NO:37:

(i) SEQUENCE CHARACTERISTICS:
        (A) LENGTH: 12 amino acids
        (B) TYPE: amino acid
        (C) STRANDEDNESS: single (D) TOPOLOGY: linear (ii) MOLECULE TYPE: polypeptide (xi) SEQUENCE DESCRIPTION: SEQ ID NO:37:

Arg Tyr Ile Leu Arg Gly Ile Ser Ala Leu Ar
g Lys
1               5
                        10

(2) INFORMATION FOR SEQ ID NO:38:

(i) SEQUENCE CHARACTERISTICS:
            (A) LENGTH: 12 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:38:

Gly Asp Gln Tyr Lys Ser Val Leu Met Val Se
r Ile
1               5
                        10

(2) INFORMATION FOR SEQ ID NO:39:

(i) SEQUENCE CHARACTERISTICS:
            (A) LENGTH: 12 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:39:

Gly Asp Gln Tyr Arg Ser Val Leu Met Val Se
r Ile
1               5
                        10

(2) INFORMATION FOR SEQ ID NO:40:

(i) SEQUENCE CHARACTERISTICS:
            (A) LENGTH: 16 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:40:

Ala Gly Ile Leu Lys Ile Asn Phe Leu Ile As
n Lys Met Gln Glu Asp
1               5
                        10
                                15

(2) INFORMATION FOR SEQ ID NO:41:

(i) SEQUENCE CHARACTERISTICS:
            (A) LENGTH: 16 amino
acids
            (B) TYPE: amino acid
            (C) STRANDEDNESS: single
            (D) TOPOLOGY: linear (ii) MOLECULE TYPE: polypeptide (xi) SEQUENCE DESCRIPTION: SEQ ID NO:41:

Ala Gly Ile Leu Arg Ile Asn Phe Leu Ile As
n Lys Met Gln Glu Asp
1               5
                    10
                        15

(2) INFORMATION FOR SEQ ID NO:42:

(i) SEQUENCE CHARACTERISTICS:
        (A) LENGTH: 11 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:42:

Asn Met Leu Arg Lys Leu Arg Asp Ala Phe Se
r
1               5
                    10

(2) INFORMATION FOR SEQ ID NO:43:

(i) SEQUENCE CHARACTERISTICS:
        (A) LENGTH: 11 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:43:

Asn Met Leu Arg Arg Leu Arg Asp Ala Phe Se
r
1               5
                    10

(2) INFORMATION FOR SEQ ID NO:44:

(i) SEQUENCE CHARACTERISTICS:
        (A) LENGTH: 12 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:44:

Phe Leu Leu Lys Cys Leu Lys Gln Val Arg Ly
s Ile
1               5
                    10

(2) INFORMATION FOR SEQ ID NO:45:

(i) SEQUENCE CHARACTERISTICS:
        (A) LENGTH: 12 amino
acids
        (B) TYPE: amino acid
        (C) STRANDEDNESS: single
        (D) TOPOLOGY: linear (ii) MOLECULE TYPE: polypeptide (xi) SEQUENCE DESCRIPTION: SEQ ID NO:45:

-continued

```
Phe Leu Leu Lys Cys Leu Arg Gln Val Arg Ly
s Ile
1               5
                10

(2) INFORMATION FOR SEQ ID NO:46:

(i) SEQUENCE CHARACTERISTICS:
          (A) LENGTH: 14 amino
acids
          (B) TYPE: amino acid
          (C) STRANDEDNESS: single
          (D) TOPOLOGY: linear (ii) MOLECULE TYPE: polypeptide (xi) SEQUENCE DESCRIPTION: SEQ ID NO:46:

Tyr Leu Leu Glu Ala Lys Lys Ala Glu Asn Il
e Thr Thr Gly
1               5
                10

(2) INFORMATION FOR SEQ ID NO:47:

(i) SEQUENCE CHARACTERISTICS:
          (A) LENGTH: 14 amino
acids
          (B) TYPE: amino acid
          (C) STRANDEDNESS: single
          (D) TOPOLOGY: linear (ii) MOLECULE TYPE: polypeptide (xi) SEQUENCE DESCRIPTION: SEQ ID NO:47:

Tyr Leu Leu Glu Ala Lys Arg Ala Glu Asn Il
e Thr Thr Gly
1               5
                10
```

We claim:

1. A granulocyte-macrophage colony-stimulating factor (GM-CSF) antagonist comprising an unglycosylated GM-CSF wherein one or more amino acids of said GM-CSF which are exposed in a first α-helix and have acidic properties are substituted with a basic amino acid residue.

2. The GM-CSF antagonist according to claim 1 wherein the GM-CSF is of human, livestock animal, companion animal or laboratory test animal origin.

3. The GM-CSF antagonist according to claim 2 wherein the GM-CSF is of human origin.

4. The GM-CSF antagonist according to claim 1 wherein the acidic amino acid residue on the first α-helix is Glu and/or Asp and the basic amino acid residue substituted therefor is Arg and/or Lys.

5. An agent comprising one or more of said GM-CSF antagonists as defined in claim 1 for treating the aberrant effects of an endogenous GM-CSF.

6. A pharmaceutical composition comprising one or more GM-CSF antagonists as defined in claim 1 and at least one of an acceptable carrier and diluent.

7. A GM-CSF antagonist comprising an unglycosylated modified GM-CSF, wherein the first α-helix of said GM-CSF has the amino acid sequence His Val Asn Ala Ile Gln Xaa Ala Arg Arg Leu Leu Asn Leu wherein Xaa is a basic amino acid, selected from the group consisting of Arg and Lys and wherein said modified GM-CSF is in unglycosylated form and acts as an antagonist for at least one property of native GM-CSF.

8. The GM-CSF antagonist according to claim 7 wherein Xaa is Arg.

9. A human GM-CSF antagonist comprising an unglycosylated modified human GM-CSF having an amino acid sequence in a first α-helix comprising:

(i) His Val Asn Ala Ile Gln Arg Ala Arg Arg Leu Leu Asn Leu; or (ii) His Val Asn Ala Ile Gln Lys Ala Arg Arg Leu Leu Asn Leu.

* * * * *